(12) United States Patent
Davis

(10) Patent No.: US 7,040,895 B2
(45) Date of Patent: May 9, 2006

(54) VACUUM-SEATED DENTURES WITH SKIN CONTACTING PLATE

(76) Inventor: Jesse L. Davis, 6122 S. Green St., Chicago, IL (US) 60621

( * ) Notice: Subject to any disclaimer, the term of this patent is extended or adjusted under 35 U.S.C. 154(b) by 56 days.

(21) Appl. No.: 10/923,463

(22) Filed: Aug. 20, 2004

(65) Prior Publication Data

US 2006/0040235 A1    Feb. 23, 2006

(51) Int. Cl.
*A61C 13/24*   (2006.01)
(52) U.S. Cl. .................................................. 433/185
(58) Field of Classification Search ............... 433/184, 433/185, 188
See application file for complete search history.

(56) References Cited

U.S. PATENT DOCUMENTS

| | | | | |
|---|---|---|---|---|
| 506,762 A | * | 10/1893 | Ahrens | 433/185 |
| 912,026 A | * | 2/1909 | Powers | 433/185 |
| 986,736 A | * | 3/1911 | McNinch | 433/185 |
| 1,177,979 A | * | 4/1916 | Wilson | 433/185 |
| 1,887,970 A | * | 11/1932 | Valbuena | 433/185 |
| 2,897,594 A | * | 8/1959 | Kopec et al. | 433/185 |
| 3,409,985 A | * | 11/1968 | Graceffo | 433/185 |
| 3,750,287 A | * | 8/1973 | Bloom | 433/185 |
| 3,787,974 A | * | 1/1974 | Gaylord | 433/185 |
| 4,583,949 A | * | 4/1986 | Heartness | 433/185 |
| 4,595,364 A | * | 6/1986 | Kusano et al. | 433/185 |

FOREIGN PATENT DOCUMENTS

| | | | |
|---|---|---|---|
| DE | 38 36 885 A1 | * | 5/1990 |
| GB | 1 356 556 | * | 6/1974 |
| JP | 10-99350 | * | 4/1998 |
| JP | 2004-180832 | * | 7/2004 |

* cited by examiner

*Primary Examiner*—Ralph A. Lewis
(74) *Attorney, Agent, or Firm*—Donald W. Meeker

(57) ABSTRACT

A skin contacting plate is formed in the shape of the gums to which the plate is secured by a skin adhering compound on a perforated layer. A protruding ridge along the teeth line has an internal reservoir to receive a skin adhering compound solvent from a syringe-type liquid pump to dissolve the compound to remove the skin contacting plate when desired. A denture plate conforms to the shape of the skin contacting plate and the protruding ridge. A syringe-type vacuum air pump draws the air from between an internal passageway between the plates through a valve in the denture plate to form a vacuum to maintain the plates together. Pumping air into the internal passageway immediately releases the plates.

7 Claims, 1 Drawing Sheet

VACUUM-SEATED DENTURES WITH SKIN CONTACTING PLATE

BACKGROUND OF THE INVENTION

1. Field of the Invention

The present invention relates to dentures that are held in place with a vacuum seal, and particularly to dentures with a plate secured to the gums with an adhering compound brushed onto a perforated metal bottom of the plate and an insertable vacuum pump air which draws air out of an internal passageway in the dentures through an automatically sealable air valve in the dentures to evacuate the air from the space between the plate and the dentures creating a strongly attractive vacuum to firmly secure the dentures in place.

2. Description of the Prior Art

Dentures are substitutes for missing teeth and serve as a replacement for all or some of the teeth found in the oral cavity. Despite diligent efforts by dental professionals and designers of dental prostheses, dentures do not always fit perfectly. Adherent creams, liquids or powders are often used to secure or temporarily fix dentures within the mouth.

U.S. Pat. No. 4,595,364, issued Jun. 17, 1986 to Kusano, provides a dental prosthesis having artificial teeth, a denture base made of a hard polymer material and an elastic-lining layer provided on an inner surface of the denture base. The prosthesis comprises a recess portion provided on the elastic-lining layer for forming a sealed chamber, a small bore for communicating the sealed chamber with an exterior, a check valve member for exhausting air in the chamber from the recess portion to the exterior, and a member for preventing an alveolar gingiva from projecting into the recess portion. The dental prosthesis can be stably and steadily supported on an alveolus ridge of a patient.

U.S. Pat. No. 4,583,949, issued Apr. 22, 1986 to Heartness, shows a partial vacuum stabilizer for dental prosthesis. The dental prosthesis secures to the alveolar ridge within the mouth of the user through the application of a partial vacuum, which serves to stabilize and maintain a dental plate in secure operative position. A full or partial dental plate incorporates false teeth at least some of which have a hollow interior portion in which valve means are mounted in fluid communication with a pressure differential channel itself extending along and being disposed in fluid communication with exposed surface portions of the alveolar ridge. Application of negative pressure to the interior of the mouth serves to direct fluid flow from the differential pressure channel through the valving structure within the hollow interior portion wherein such valving structure prohibits reverse flow therethrough. A partial vacuum is thereby created and maintained between the undersurface of the dental plate, in the area of the differential pressure channel, and the exposed surface of the alveolar ridge.

U.S. Pat. No. 4,204,322, issued May 27, 1980 to Johnson, claims an apparatus for securing a denture plate in position. The illustrated and preferred embodiment incorporates a vacuum pump, which has the exterior form and shape of a tooth embedded in a denture plate. The tooth incorporates a reciprocally operated pump. The pump pulls air from an exposed, lower indention or chamber. This chamber is connected via multiple passages to similar chambers around the denture, all of the chambers collectively open to the gum of the wearer. As air is evacuated from the chambers, a vacuum is formed. The vacuum increases holding power of the denture against the gum.

U.S. Pat. No. 3,787,974, issued Jan. 29, 1974 to Gaylord, describes a unit molded into a denture that includes a casing forming a pumping chamber in the denture and being open toward the exposed side if the denture with conduits connecting two receptacles in a suction chamber or chambers, which latter are open toward the gum side of the denture. The denture also comprises a resilient pumping element in the pumping chamber that is adapted to produce suction in each receptacle. At each receptacle is an enlarged suction cavity and a suction head secured in the receptacle projects into the suction cavity and has holes in its sides communicating through the receptacle with the conduits, whereby when by suction the system is filled with a fluid, and then placed over the gum, some of the moisture is expelled by the pumping means, which when released produces a predetermined suction to suck the gum into the cavity and around the suction head. The suction head is replaceable by a cavity forming element that has a suitable wire adapted to be extended through the form of the gum on which the denture is molded, thereby to assist in holding the unit in position during the molding, and also in forming the cavity.

U.S. Pat. No. 3,750,287, issued Aug. 7, 1973 to Bloom, discloses a valving device for use with dental prosthesis. The device includes a sleeve of a length in excess of the width of the wall of a dental plate in which the same is to be imbedded or contained and a valve structure retained within the sleeve for subsequent removal and substitution therefor by a new valve structure.

U.S. Pat. No. 3,555,683, issued Jan. 19, 1971 to Gregorovic, indicates a dental prosthesis with a valve and a vacuum chamber, which is characterized in that the valve is made of rust-proof material and has a rigid outer member and a movable assembly with a stopper for preventing penetration of foreign bodies and a seal for maintaining the vacuum. The stopper and the seal are applied against respective seatings by spring means. The vacuum chamber is of smaller cross-section in the portions thereof lying within the extension of the incisor and canine teeth than it is in the portions thereof located opposite the molars.

U.S. Pat. No. 3,409,985, issued Nov. 12, 1968 to Graceffo, puts forth denture devices with suction check valve means, which are operable by the user. The suction check valves may be adjusted to regulate the degree of negative pressure of vacuum to suit the comfort of the user. The check valves are spring-biased to their closed positions or which are closed and held closed by the force of gravity.

U.S. Pat. No. 2,897,594, issued Aug. 4, 1959 to Kopec, concerns a denture with a check valve means. The check valves may either be located the gum enclosing ridge of the plate or in the teeth of the denture. The check valve comprises a counterbore with a thin flexible diaphragm made of rubber or other flexible material. The diaphragm has vent holes therethrough and acts as a check valve to allow air to pass out through the vent hole, but when air attempts to pass in the diaphragm will engage a bottom surface of the counterbore and form a seal thereon.

U.S. Pat. No. 2,029,945, issued Feb. 4, 1936 to Rubinstein, illustrates a denture valve construction, of which the contour facilitates placement during the construction of the denture. A denture is provided, which includes a base adapted to fit over the gum, said base having an air passageway for the withdrawal of air from between the gum and the base. The denture further comprises a hollow valve one face of which is an elastic substantially flat diaphragm normally closing said passageway, but adapted to open the same but its responsiveness to a difference in air pressure on its opposite faces created by suction induced by the user.

U.S. Pat. No. 1,887,970, issued Nov. 15, 1932 to Valbuena, is for a dental plate with a plurality of supporting projections located within the suction or vacuum chamber of the dental plate, which are adapted to conform with the shape of the corresponding tissue of the mouth. The tips of the projections prevent gum or soft tissue from being drawn into the suction chamber. The dental plate also comprises a valve construction that will create the desired negative pressure within the vacuum chamber and prevent leakage to the same so that practically no attention need be given to the plate by the wearer after its installation.

U.S. Pat. No. 1,696,110, issued Dec. 18, 1928 to Döbele, provides a dental plate with a sucker, which comprises a dental plate having a cavity, a membrane holder embedded in the plate, and a suction membrane retained between the holder and the plate. The membrane has a perforation in the portion exposed through the opening in the holder, said perforation being adapted to open to permit withdrawal of air from the cavity and being self-closing to prevent the subsequent return of air to said cavity.

U.S. Pat. No. 1,337,622, issued Apr. 20, 1920 to Reese, shows a vacuum-suction dental plate. The plate is preferably provided with a depression in its upper surface intended to form initially a vacuum chamber from which the air is exhausted. An opening is provided in the plate, which in said opening is mounted a valve casing, preferably constructed of non-corrodible metal an provided with a flanged edge adapted to grip the edge of the opening in the plate. The underside of the valve casing is cut away to permit easy insertion and withdrawal of the valve which is provided with a central opening. The thickness of the valve is slightly less than the distance between the opposite walls of the valve casing, the upper wall of which is provided with an opening adjacent the periphery of the valve. Air may be exhausted from the space between the plate, denture, or other device and the adjacent tissue of the mouth.

U.S. Pat. No. 1,184,187, issued May 23, 1916 to Linares, claims an artificial denture with a seating to engage the tissue of the mouth, which has an air passage extending through from the suction surface of the seating to the opposite face of the denture, and a suction device located in the air passage and adapted when pressed to expel from between the seating of the denture and the tissue on which it rests. The artificial denture further comprises a movable piston, which can be located in place of one of the artificial teeth, which when pressed will expel the air located the seating of the denture and the tissue on which it rests.

U.S. Pat. No. 1,177,979, issued Apr. 4, 1916 to Wilson, describes a suction holding means for dental plates, which comprises a valve out of the reach of the wearer's tongue. The valve is also lies in direct line of the suction, whereby in the upper plate it will lie in a horizontal rearwardly extending direction, but in the lower plate it will lie in a nearly vertical direction. Once the air is expelled, the valve is closed by means of a spring.

U.S. Pat. No. 986,736, issued Mar. 14, 1911 to McNinch, discloses a suction-air chamber for dental plates which comprises two parts, the first part the artificial palate, having female member vulcanized therein. The second part includes a soft-rubber air chamber having an outlet, over which is placed a perforated soft rubber diaphragm, which acts as a valve for closing the outlet. The air chamber has a male member mounted thereon, which snaps into the female member, thereby detachably securing the second part to the first part. The construction of the suction air chamber permits the air that remains in the chamber, after it has been placed in the mouth to be readily withdrawn, so that a vacuum will be obtained, thereby causing the air chamber to collapse and rest against the roof of the mouth, which will draw the artificial palate securely into place. The air chamber, being detachable, may be replaced when worn out.

U.S. Pat. No. 912,026, issued Feb. 9, 1909 to Powers, indicates a dental suction-plate that comprises a dental plate having a cup received in a recess in the plate, said cup having an opening therein extending through the plate and grooves leading to the opening, a valve received in the cup, and an annular channel formed in the cup for holding the valve therein.

U.S. Pat. No. 795,084, issued Jul. 18, 1905 to White, puts forth an artificial upper denture provided with a screw-threaded opening, a screw-threaded plug engaging the opening, and provided with a longitudinal air passage opening below the upper face of the denture and means below the plate whereby the plug may be turned in the opening. A suction tube device is provided for engagement with the threaded opening. The suction pump tube is threadingly connected to the opening and the air removed from between the plate and the adjacent tissues of the mouth. The suction tube is then removed and the opening is closed with the screw-threaded plug or alternately with amalgam.

U.S. Pat. No. 506,762, issued Oct. 17, 1893 to Ahrens, concerns a process of securing dental suction valves to plates, which consists of first enclosing the edges and part of the side of the valve in metal, next cementing the rubber disk to the mouth cast or mold exactly in the position called for by the shape of the mouth, then placing the plate in position on the valve and vulcanizing the two together.

U.S. Pat. No. 317,667, issued May 12, 1885 to Parker, illustrates a dental plate with three air chambers and a passage through the plate, whereby the air between the plate and the mouth may be completely and readily exhausted. A valve is provided which allows the passage of air from the chambers, but prevents reentry of air into the chambers.

What is needed is pre-attached plates (which may use a skin adhering compound) conforming to the shape of the gums and adhered to the gums and vacuum dentures applied to the plates to create a strong vacuum to firmly secure the dentures in place.

SUMMARY OF THE INVENTION

An object of the present invention is to provide pre-attached plates (which may use a skin adhering adhesive) conforming to the shape of the gums and adhered to the gums and vacuum dentures applied to the plates to create a strong vacuum to firmly secure the dentures in place.

Another object of the present invention is to provide a perforated metal bottom surface on the plate with adhesive brushed on to create a secure bonding between the plate and the gums, and a reservoir in the plate into which an adhesive solvent is injected with a syringe to dissolve the solvent attaching the plate to the gums for removing the plate from the gums.

One more object of the present invention is to provide an air space and automatically sealing valve in the dentures to permit insertion of a hand pump through the valve to draw out the air between the dentures creating a strong vacuum securing the dentures in place and to inject air between the dentures and the plate through the valve for easy removal of the dentures when desired.

An additional object of the present invention is to provide a relatively easy system to use with a simple hand and finger operated syringe-type pump inserted through the self sealing valves for both injection of the adhesive solvent to the plate and the vacuum to seal the dentures to the plate or air to release the dentures from the plate with simple steps.

In brief, a plate is molded from an impression of the gums to conform to the shape of the gums. The plate is secured to the gums with a skin adhering compound brushed onto a perforated metal bottom of the plate. An insertable vacuum pump, preferably a syringe-type hand and finger operated pump with a pointed tip, draws air out of an internal passageway between the dentures and the plate through an automatically sealable air valve in the dentures to evacuate the air from the space between the plate and the dentures creating a strongly attractive vacuum to firmly secure the dentures in place. To remove the dentures, the same pump is inserted in the valve and air injected between the dentures and the plate for easy removal of the dentures.

An advantage of the present invention is that it provides pre-attached plates conforming to the shape of the gums and adhered to the gums and vacuum dentures applied to the plates to create a very strong vacuum, not possible between the dentures and the gums, to firmly secure the dentures in place.

Another advantage of the present invention is that it provides a secure bonding between the plate and the gums by a skin adhering compound on a perforated plate.

One more advantage of the present invention is that it provides easy secure installation and removal of the dentures to the plate with a simple hand and finger operated pump.

BRIEF DESCRIPTION OF THE DRAWINGS

These and other details of my invention will be described in connection with the accompanying drawings, which are furnished only by way of illustration and not in limitation of the invention, and in which drawings.

BEST MODE FOR CARRYING OUT THE INVENTION

Figure 1:
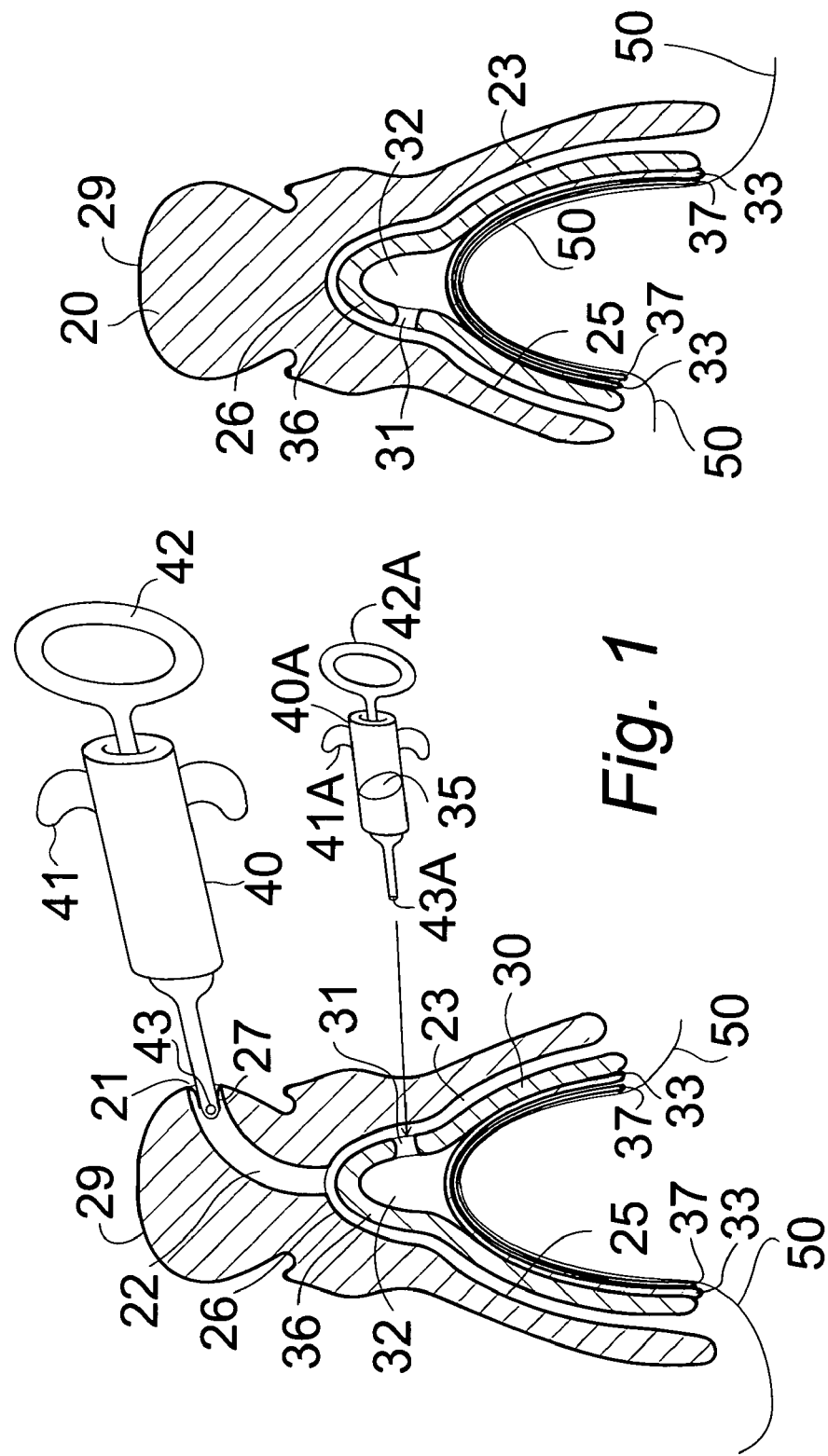
FIG. 1 is a cross-sectional view taken through the vacuum denture system of the present invention and the gums of a wearer showing the skin contacting plate, the vacuum dentures, a vacuum pump, and a pump for a skin adhering compound.
Figure 2:
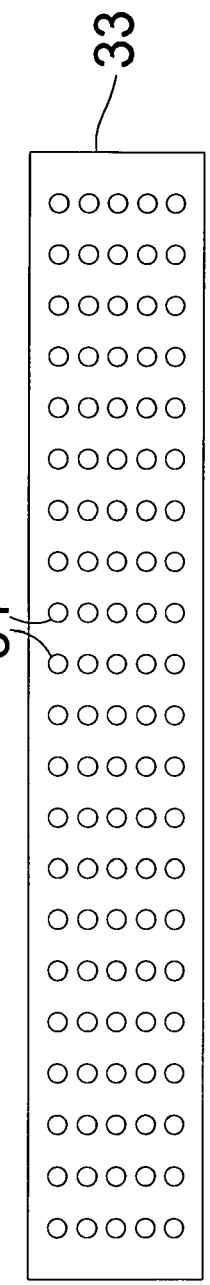
FIG. 2 is a plan view showing the pattern of air holes in a skin contacting plate of the system of FIG. 1.

In FIGS. 1 and 2, a vacuum denture system for secure attachment of dentures comprises a skin contacting plate 30 adhered to the gums 50 and a denture plate 20 secured to the skin contacting plate by a vacuum therebetween.

In FIG. 1, the skin contacting plate 30, made from a clay mold imprint of the gums, conforms to the shape of the gums 50 and is adapted for securing to the gums with a securing substance, such as a skin adhering compound 37. The skin contacting plate 30 comprises an inner layer 33 or membrane adjacent to the skin of the gums 50 of the wearer, the inner layer 33 having an array of perforations 34 through the inner layer, as seen in FIG. 2, to admit the securing substance, the skin adhering compound 37, therethrough to bond the skin contacting plate 30 to the gums 50. After spreading the skin adhesive onto the perforated bottom of the plate, pressing the plate onto the gums causes the adhesive to spread through the perforations forming little balls or caps which dry to lock the plate 33 onto the gums 50.

The skin contacting plate outer layer 30 conforms to the shape of the gum surface 50 of a wearer and preferably has a protruding ridge 36 above a gum surface at a teeth line 51 of a wearer. A reservoir 32 within the protruding ridge 36 receives a quantity of the adhesive solvent or dissolving substance 35 therein. A plate opening 31 through the skin contacting layer 30 in the protruding ridge 36 communicates with the reservoir 32. A hand-operated syringe-type liquid pump 40A containing the adhesive solvent 35 has a plunger 42A and finger grips 41A and a narrow tip with an opening 43 for discharging the adhesive solvent 35 into the plate opening 31 and into the reservoir 32 which feeds the skin adhesive solvent 35 to the inner layer 33 to dissolve the adhesive to remove the plate when desired.

A denture plate 20 comprises an outer surface 29 having a normal simulated teeth and gum structure and an inner surface 25 conforming to the shape of the skin contacting plate and adapted to form an airtight vacuum seal in the internal passageway 23 between the two plates with an inner convex surface 26 of the denture plate 20 adapted to conform to the shape of the protruding ridge 36 of the skin contacting plate for greater security in maintaining the denture plate in place. An automatically sealable air valve 27 communicates between the internal passageway 23 and an exterior of the outer surface of the denture plate through a denture plate opening 21.

A vacuum pump, preferably a syringe-type hand and finger operated air pump 40, with a plunger 42 and finger grips 41 and a rounded tip having at least one air hole 43 therein, is adapted to fit with the rounded tip in the air valve 27. The vacuum pump 40 is adapted to draw air out from the internal passageway 23 to create a vacuum between the two plates to firmly secure the two plates together and alternately adapted to pump air into the internal passageway 23 to release a vacuum in the internal passageway and separate the two plates for removal of the denture plate when desired.

It is understood that the preceding description is given merely by way of illustration and not in limitation of the invention and that various modifications may be made thereto without departing from the spirit of the invention as claimed.

What is claimed is:

1. A vacuum denture system for secure attachment of dentures, the system comprising:
    a skin contacting plate conforming to the shape of the gums, the skin contacting plate adapted for securing to the gums with a securing substance;
    a denture plate comprising an outer surface having a simulated teeth and gum structure and an inner surface conforming to the shape of the skin contacting plate and adapted to form an airtight vacuum seal in an internal passageway between the two plates, an automatically sealable air valve communicating between the internal passageway and an exterior of the outer surface of the denture plate, and a vacuum pump adapted to be insertable through the sealable air valve in the denture plate and further adapted to draw air out from the internal passageway to create a vacuum between the two plates, to firmly secure the two plates together and alternately adapted to pump air into the internal passageway to release a vacuum in the internal passageway and separate the two plates for removal of the denture plate when desired.

2. The device of claim 1 wherein the vacuum pump comprises a syringe-type hand and finger operated pump with a rounded tip having at least one air hole therein, the rounded tip adapted to fit into the air valve.

3. The device of claim 1 wherein the skin contacting plate comprises an inner layer adjacent to the skin, the inner layer having an array of perforations through the inner layer to admit the securing substance therethrough and an outer layer to receive the denture plate.

4. The device of claim 3 wherein the outer layer of the skin contacting plate further comprises a protruding ridge above a gum surface at a teeth line of a wearer and the denture plate has a mating concave recess to receive the ridge.

5. The device of claim 4 wherein the skin contacting plate further comprises a reservoir within the protruding ridge for receiving a quantity of a securing substance solvent therein for dissolving the securing substance when desired to remove the skin contacting plate.

6. The device of claim 5 wherein the skin contacting plate further comprises at least one plate opening through the skin contacting layer communicating with the reservoir, and the device further comprises a hand-operated syringe-type pump containing the securing substance solvent, the pump having a narrow tip with an opening for discharging the securing substance therethrough, the plate opening adapted for receiving the narrow tip therein to pump the securing substance into the reservoir.

7. The device of claim 1 wherein the securing substance comprises a skin adhering compound.

* * * * *